United States Patent [19]
Synder

[11] 3,991,756
[45] Nov. 16, 1976

[54] METHOD AND APPARATUS FOR INTRAVENOUS ACCESS

[76] Inventor: Donald Synder, 715 NE. 3rd Ave., Delray Beach, Fla. 33444

[22] Filed: Aug. 18, 1975

[21] Appl. No.: 605,335

[52] U.S. Cl. ............................ 128/214 R; 128/260; 128/348
[51] Int. Cl.² .......................................... A61M 5/00
[58] Field of Search ............ 128/214 R, 348, 334 C, 128/214.4, 347, 215, 221, 260, DIG. 16

[56] References Cited
UNITED STATES PATENTS

| | | | |
|---|---|---|---|
| 3,461,869 | 8/1969 | Hargest | 128/214 R |
| 3,663,965 | 5/1972 | Lee, Jr. et al. | 128/214 R X |
| 3,752,162 | 8/1973 | Newash | 128/348 |
| 3,783,868 | 1/1974 | Bokros | 128/260 |
| 3,826,256 | 7/1974 | Smith | 128/348 |

*Primary Examiner*—Stephen C. Pellergrino
*Attorney, Agent, or Firm*—Bauer, Amer & King

[57] ABSTRACT

Repeated single needle access to the vascular system is accomplished without percutaneous needling of the skin. A cannula is surgically implanted adjacent to a selected artery or vein and interfaces with same along a longitudinal wall. One end of the cannula exits from the skin. Needle means including an indexing scheme allows serial puncturing of the interface wall to thereby provide the vascular access. When not in use the cannula is plugged and the exposed end thereof is covered preferably by an elastic layer.

23 Claims, 7 Drawing Figures

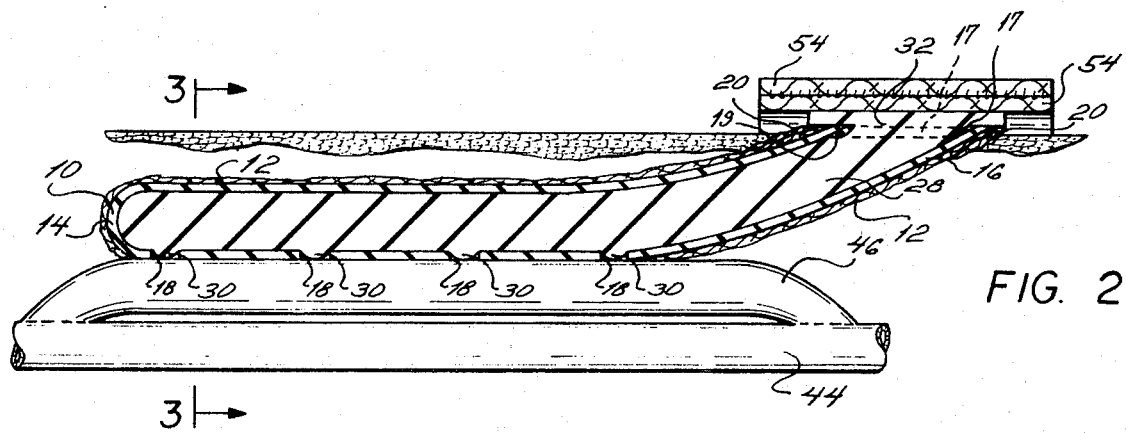
FIG. 1
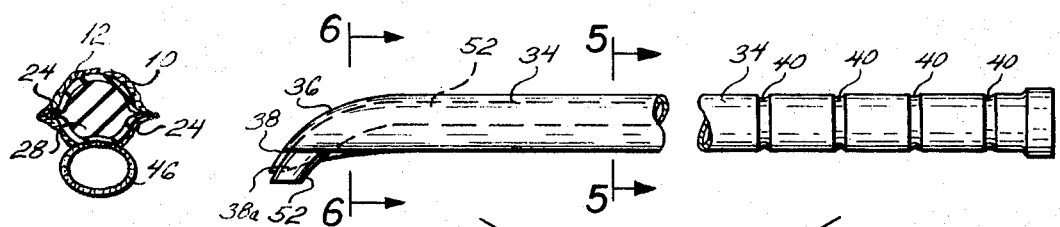
FIG. 2
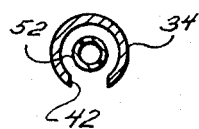
FIG. 3
FIG. 4
FIG. 5   FIG. 6
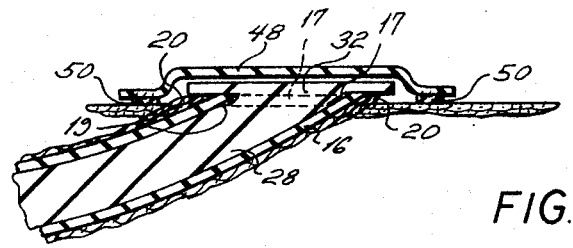
FIG. 7

METHOD AND APPARATUS FOR INTRAVENOUS ACCESS

FIELD OF INVENTION

This invention relates to a method and apparatus for repeated single needle access to the vascular system without percutaneous needling of the skin.

BACKGROUND OF THE INVENTION

Many situations arise where it is necessary to tap fluid into or out of veins or arteries. To do so and for example, during conventional intravenous feeding it may be necessary to inject and withdraw a needle several times. Normally such a procedure requires repeated percutaneous needling of the skin. Further, a patient requiring hemodialysis would need many such needlings. Thus a significant drawback in hemodialysis as is presently practiced is the fact that communication with the appropriate veins must be maintained for repeated periods of short durations over what may be the life of the patient. It is readily apparent that there are significant drawbacks associated with this approach. Not the least of these is the fact that continued reinsertion and breaking of the skin leads to the scarring thereof, causes a "blueing" of the skin on that body portion adjacent the punctures leaving the patient prone to bacterial infection. Further still, continued repuncturing of the skin is painful and may have adverse psychological consequences.

Several approaches are currently utilized to provide vascular access during hemodialysis. In one approach, two needles are inserted into the patient's veins wherein the needles are coupled to an appropriate artery by means of a fistula. An advance over this method utilizes a single needle approach and a phase-shift pressure regulator pumping system for dialysis. While this last mentioned single needle approach is an improvement over the two needle scheme, it still requires continued percutaneous needling of the skin and dilated veins each time the patient is dialysised.

SUMMARY OF INVENTION

The present method and apparatus is designed to provide percutaneous access to the vascular system without percutaneous needling of the skin. The inventive device remains in position internally as long as the patient requires hemodialysis or other continued percutaneous access to the vascular system. To accomplish this, the present invention provides for silastic cannula having a dacron cover of specific design that is surgically implanted in an extremity of the patient. The cannula is positioned so as to juxtapose along an interface wall with an arterial bypass. The cannula is in effect a tube having one end closed and the other end open. A longitudinal segment of the cannula forms the interface wall and communicates with the arterial bypass. The open end of the cannula exits through the skin and is attached thereto by a cyanoacrylate tissue adhesive thus forming an exit site.

A stainless steel needle of sufficient size to accept 14-gauge catheter is adapted to slide through the cannula. One end of the needle has a unique flared tip having a blade portion. Further, the needle is formed with a longitudinal slot along its length and the other end of the needle shaft is fitted with detents that correspond to the location of the needle tip. The detents interdigitate with an internal ring at the exit or exposed part of the cannula. The hub of the needle is a conventional luer-lock arrangement. The needle is inserted into the cannula and rotated approximately 90° about its longitudinal axis so that the tip thereof punctures the vessel wall. The catheter is then inserted into the needle and guided into the arterial bypass through the needle tip. The needle is then withdrawn from the cannula and from around the catheter. As the needle is removed, the catheter slips through the needle's longitudinal slot allowing the catheter to remain in place. Each detent mark corresponds to a different location of the needle tip providing several points of access through the arterial bypass. Serial use of the detent structure allows the punctured tissue time to heal before it is repunctured during a subsequent dialysis.

When not in use the cannula is closed by a complimentary insert or trocar and attached plug with the plug covering the cannula open end. An elastic covering is placed over the plug and glued to the skin to cover the exit site.

OBJECTS OF THE INVENTION

It is therefore an object of the present invention to provide a method and apparatus for intravenous communication.

It is another object of the present invention to provide a method and apparatus permitting repeated percutaneous access to the vascular system without percutaneous needling of the skin.

It is a further object of the present invention to provide percutaneous access to the vascular system by means of a cannula that remains with the patient for as long as such access is required.

It is a still further object of the present invention to provide a method of communicating with the vascular system and that does so without requiring repeated puncturing of the patient's skin.

It is yet another object of the present invention to provide a method and apparatus that permits insertion of a catheter into a selected artery or vein at predetermined points whereby in the event that repeated insertions are required, the previous punctured tissue is allowed time to heal.

It is still another object of the present invention to provide a means for communicating with the vascular system by means of a cannula wherein a portion thereof remains with and is imbedded in the patent while another portion thereof resides on the skin surface and includes means for sealing the latter portion to prevent contamination thereof.

It is yet a further object of the present invention to provide a cannula that permits single needle dialysis therethrough with means provided to prevent blood flow into the cannula when the same is not in use.

Other objects and features of the present invention will become apparent from the following detailed description considered in connection with the accompanying drawings. It is to be understood, however, that the drawings are designed for purposes of illustration only and not as a definition of the limits of the invention for which reference should be made to the appending claims.

BRIEF DESCRIPTION OF THE DRAWING

In the drawings, wherein the same reference numeral denotes the same element throughout the several views:

FIG. 1 is a perspective view in section of the inventive cannula showing an aperture scheme thereof on which the needle tip aligns and through which the catheter passes;

FIG. 2 is an elevational view of the inventive cannula showing the trocar with integral plug in the cannula with the cannula sutured on to the arterial bypass, the open end of the cannula is seen projecting from and attached to the surface of the skin;

FIG. 3 is a view along the line 3—3 of FIG. 2 and seen in direction of the arrows indicating the semicircular shape a portion of the cannula wall assumes as it interfaces against the arterial bypass;

FIG. 4 is an elevational view of the needle showing one end of the needle having a tip portion that is flared in relation to the needle body and the other with the catheter operatively placed therein;

FIG. 5 is a sectional view along the line 5—5 of FIG. 4 and looking in direction of the arrows and showing the longitudinal slot along the needle;

FIG. 6 is a sectional view along the line 6—6 of FIG. 4 and looking in direction of the arrows; and FIG. 7 shows one method of sealing the open end of the cannula by means of the trocar plug and an elastic band on the patient's extremity, the band is shown positioned over the plug and cannula to protect same from dislocation.

DETAILED DESCRIPTION OF THE DRAWINGS

Referring now to the drawings, a tubular cannula 10 is made of silastic material and is defined by a Dacron mesh cover 12. The intertestecies of the Dacron mesh permits tissue to grow into the intertestecies thereof and the mesh permits the cannula to be sutured in place as will be described hereinafter. One end 14 of the cannula is closed, while the other end 16 is open. Open end 16 of cannula 10 is preferably defined by a hardened ring 17 from which projects a button or lock element 19. An aperture scheme defined by a plurality of apertures 18 is disposed through a wall portion of the cannula with each of the apertures at a different distance from end 14 as shown. The other and open end of cannula 10 includes a Dacron felt cuff 20 the operation of which will be likewise described hereinafter. Along the internal peripheral surface of the cannula there is disposed one or a pair of opposed longitudinal grooves 24 paralleling the aperture scheme, and shown in FIG. 1. Further, a plurality of spaced annular grooves 26 are formed on the inside of the cannula periphery each transverse to and intercepting longitudinal groove 24 and a respective aperture 18.

A trocar 28 comprising a silastic rod is sized sufficiently so as to lightly interferingly engage with the interior of cannula tube 10 when pushed thereinto. Hence, as trocar 28 is pushed into the cannula through open end 16, the trocar completely fills and occludes the cannula interior. Trocar 28 carries a plurality of nub-like excresences 30 on its surface. The excresences are in registration with the aperture scheme so that when the trocar is inserted in the cannula, excresences 30 fit into an associated aperture 18 to substantially close the same. Trocar 28 further includes an integral plug portion 32 that fits into and seals end 16 of the cannula when the trocar is inserted therein during operation of the inventive device as will be described.

A stainless steel needle 34 has an outside diameter sized to fit in cannula 10 and has a hollow interior sized sufficiently to accept a 14-gauge catheter. One end of the needle is formed with a beak-like tip 36 from which depends a blade extension 38 having a cutting edge or blade 38a. As will be seen in FIG. 4 tip portion 36 flares outwardly with respect to the body portion proper of needle 34. The other end of needle 34 carries a detent scheme 40 with the spacing between the detents corresponding to the relative spacing between apertures 18. Further and as seen in FIGS. 5 and 6 needle 34 is formed with a longitudinal slot 42 that runs the length of the needle.

Operation of the inventive apparatus is as follow: The surgical procedures involved in use of the inventive cannula and needle may vary depending on the particular anatomical problems that exist. While the foregoing discussion shows use of the inventive cannula on an arterial bypass, it is to be understood that the cannula may be attached directly to the surface of the artery and its accompanying subcutaneous tissue. In the arterial bypass scheme, a suitable artery 44 is chosen. By a conventional surgical procedure, an arterial bypass 46 is attached thereto. Thus, a portion of the blood that would normally flow through artery 44 is routed through bypass 46. Cannula 10 with dacron covering 12 is sutured onto the subcutaneous tissue surrounding bypass 46 with the attachment substantially as shown in FIG. 2. When so attached, that portion of the cannula wall containing aperture scheme 18 is junxtaposed against a portion of the arterial bypass thereby to define an interface region or interface wall between the cannula and the arterial bypass. As seen in FIG. 3, that portion of the cannula which is opposed to the arterial bypass deforms so as to be complimentary with and accommodate the periphery of the arterial bypass to thereby define this interface region.

End 16 of cannula 10 projects from the surface of the skin and is adhesively attached thereto with a fast acting cyanoacrylate tissue adhesive. As shown in FIG. 7 the procedure for forming this exit site is accomplished by adhesively securing felt cuff 20 to the skin immediately adjacent thereto. The intertestices of the cuff accommodate ingrowth of fibroblasts so that after several days the cannula exit site is securely implanted in the skin. Immediately after the surgical implantation operation it may be advantageous to isolate the exit site from ambient surroundings and this may be accomplished by an antiseptic collar or ring, the collar not shown, complimentary with the periphery of cannula end 16 and riding on the skin surface.

Trocar 28 is inserted into the cannula so that plug portion 32 is frictionally held within end 16 by action of lightly interfering engagement therewith. One method for protecting the exit site is as follows. An elastic covering or cap 48 having a peripherial region carrying VELCRO portions is positioned over the exit site and detachably held thereto by having the cap's VELCRO portions interengage with an elastic VELCRO band 50 on the patient's extremity and positioned about the exit site. In another protective scheme, a wide VELCRO band, the wide band not shown, is merely wrapped about the site to protect same from dislocation.

In use, and in the embodiment shown, covering 48 is removed, trocar 28 is withdrawn from the cannula by pulling on plug portion 32. The trocar and integral plug are then placed and stored in a remote sterilizing solution. The area surrounding the exit site is prepared by treating it with a sterilizing solution. The empty cannula is now flushed with a saline solution in an aseptic manner. Needle 28 which has been sterilized is now inserted in cannula 10 with tip portion 26 being guided by longitudinal groove 24. The needle is pushed into the cannula until the needle tip engages a selected annular groove 26. The selection is accomplished by positioning projection 19 in an associated dentent 40 thereby to position needle tip 38 in registration with the selected one of annular grooves 26. Needle 34 is then rotated 90° about its longitudinal axis which action in combination with annular groove 26 guides needle tip 38 into the aperture 18 associated with the selected groove 26. Once the needle is rotated 90°, tip 38 is now oriented over or slightly in aperture 18 at which time the needle is pushed slightly forward and downwardly. This causes tip 38 to fully enter aperture 18 whereby continued forward driving of the needle causes blade 38a to cut the vessel wall of bypass 46 immediately under the selected aperture. A catheter 52 having a blunt nose and a beveled tip is inserted in needle 34 through slot 42. As the catheter is pushed into the needle, the needle guides the catheter while the same moves along the needle interior. The catheter, seen in phantom in FIGS. 4, 5 and 6, is guided along the interior of the needle until it enters that portion of the needle in the aperture and cannula, and strikes the inside face or wall of nose portion 36. Since needle nose 36 is angled downwardly, it likewise displaces the catheter tip downwardly causing the same to pass through both aperture 18 and the now punctured vessel wall. Continued pushing on the catheter causes it to enter the arterial bypass. The needle is subsequently removed by carefully working it in relation to the catheter which action allows the catheter to slip through longitudinal slot 42 as the needle is withdrawn from the cannula. The catheter is then attached to a single needle pumping system, the system not shown, for hemodialysis or other appropriate treatment. At the completion of dialysis, if such be the case, the catheter is withdrawn from cannula 10. Trocar 28 is then reinserted into the cannula placing the excresences thereof over and closing apertures 18. Cap 32 of the trocar is caused to interferingly engage in cannula end 16 detachably locking and sealing the trocar in the cannula. In the embodiment shown, covering 48 is then replaced over the exit site by causing the VELCRO portions of the cover to interlock with the complimentary VELCRO portions on elastic band 50. During the next hemodialyic treatment the above procedure is repeated though it is apparent that a different one of detents 40 is selected and caused to detachably lock on projection 19 so that upon on rotating the needle about its longitudinal axis, an appropriate annular groove will guide needle tip 38 into a different aperture 18. This construction permits the serial use of the several apertures allowing a given puncture to heal before the same needs to be repunctured.

While only a few embodiments of the present invention have been shown and described, it is to be understood that many changes and modifications may be made hereto without departing from the spirit and scope hereof.

What is claimed is:
1. A single needle access portal to provide intravenous communication comprising,
   a cannula: means for attaching said cannula attached to a selected artery or vein with one portion of said cannula exiting from the skin,
   needle means having a tip and adapted for insertion in said cannula, and
   means to selectively locate said needle tip along the interior of said cannula whereby driving said needle tip through said cannula and into the selected vein or artery achieves percutaneous access to the vascular system without repeated percutaneous needling of the skin.
2. The portal of claim 1, a catheter adapted for insertion in said needle means to be guided thereby into the selected and punctured artery or vein.
3. The portal of claim 1, said cannula being attached to the selected artery or vein along an interface wall and defined by a silastic tube having a dacron cover.
4. The portal of claim 3, said cannula having an aperture scheme along the interface wall, said aperture scheme being operatively placed with respect to said needle tip locating means to allow serial percutaneous access through the interface wall and into the vascular system.
5. The portal of claim 4, said needle tip locating means including a longitudinal slot along the internal periphery of said cannula, and a plurality of annular grooves formed along the internal periphery of said cannula and positioned transverse to said slot with a respective one of said grooves intercepting an associated aperture of said aperture scheme.
6. The portal of claim 1, said cannula being attached to the selected artery or vein by means of an arterial bypass.
7. The portal of claim 5, a flexible trocar substantially complimentary to the interior of said cannula and designed to detachably fit thereinto.
8. The portal of claim 7, that portion of said cannula exiting from the skin defined by a cannula hub having a dacronfelt cuff with which it is cemented to the skin.
9. The portal of claim 8, said trocar defined by nub-like excresences on its surface complimentary with and designed to fit into the aperture scheme through said cannula.
10. The portal of claim 8, said trocar including a cap adapted to detachably fit into and close said cannula end.
11. The portal of claim 10, an elastic cover detachably affixed about said cannula end to protect the same from being dislodged from the skin.
12. The portal of claim 11, an elastic band about the patient's extremity and positioned adjacent said cannula end, said band including means to detachably receive said elastic cover.
13. A method of providing percutaneous access to the vascular system without percutaneous needling of the skin comprising,
   attaching a cannula along a selected artery or vein so that the cannula interfaces the selected artery or vein along a longitudinal portion with an end of said cannula exiting the skin,
   inserting a needle having a projecting tip through said end of the cannula into the interior thereof,
   indexing selectively the needle tip with respect to said longitudinal interface, and
   driving the tip of said needle through said longitudinal interface to thereby provide access to the vascular system.
14. The method of claim 13, providing said needle with a longitudinal slot, and inserting a catheter into said needle whereby the same guides said catheter into the selected and punctured artery or vein.
15. The method of claim 14, withdrawing said needle from the cannula and while so doing allowing said cath- eter to pass through said longitudinal slot and remain coupled to the vascular system.

16. The method of claim 13, providing a plurality of apertures disposed serially along said longitudinal interface and through said cannula.

17. The method of claim 16, said selective indexing step being accomplished by providing a longitudinal slot on the interior periphery of said cannula and forming a plurality of spaced annular grooves on said cannula interior periphery with each of said grooves associated with one of said plurality of apertures, each of said annular grooves adapted to guide said needle tip into its associated one of said plurality of apertures when said needle is rotated about its longitudinal axis.

18. The method of claim 13, jacketing said cannula in a DACRON cover with said attaching step being performed by suturing said cover on the subcutaneous tissue of the selected artery or vein.

19. The method of claim 18, said attaching step being accomplished by providing a bypass on the selected artery or vein and suturing said cover to said vascular bypass.

20. The method of claim 13, glueing said cannula end to the skin tissue adjacent thereto.

21. The method of claim 16, withdrawing said catheter from said cannula and inserting a trocar into said cannula to substantially seal the same.

22. The method of claim 21, providing a cap on said trocar to cover and close said cannula end, and covering the now capped end of said cannula by means of an elastic layer.

23. The method of claim 22, said covering step being performed by attaching said elastic layer to the skin adjacent and surrounding said end of said cannula.

* * * * *

UNITED STATES PATENT OFFICE
CERTIFICATE OF CORRECTION

PATENT NO. : 3,991,756
DATED : November 16, 1976
INVENTOR(S) : DONALD SNYDER

It is certified that error appears in the above—identified patent and that said Letters Patent are hereby corrected as shown below:

Column 5, line 64, delete ":" and insert --,--
delete "attached"

Column 6, line 34, insert a hyphen (-) between dacron and felt

Signed and Sealed this

Twenty-fifth Day of January 1977

[SEAL]

Attest:

RUTH C. MASON
*Attesting Officer*

C. MARSHALL DANN
*Commissioner of Patents and Trademarks*